United States Patent [19]

Meidert et al.

[11] 4,226,997
[45] Oct. 7, 1980

[54] 8-CHLORO-5,6,7,8-TETRAHYDRO-2-QUINOLONE AND 8-BROMO-5,6,7,8-TETRAHYDRO-2-QUINOLONE, THE HYDROCHLORIDE OR HYDROBROMIDE THEREOF AND PROCESS FOR THEIR MANUFACTURE

[75] Inventors: Helmut Meidert, Frankfurt am Main; Werner H. Müller, Eppstein; Wilfried Pressler, Kelkheim, all of Fed. Rep. of Germany

[73] Assignee: Hoechst Aktiengesellschaft, Frankfurt am Main, Fed. Rep. of Germany

[21] Appl. No.: 75,240

[22] Filed: Sep. 13, 1979

[30] Foreign Application Priority Data

Sep. 16, 1978 [DE] Fed. Rep. of Germany ....... 2840437

[51] Int. Cl.³ .......................................... C07D 215/22
[52] U.S. Cl. ................................... 546/157; 260/155
[58] Field of Search ........................................ 546/157

[56] References Cited

U.S. PATENT DOCUMENTS

| | | | |
|---|---|---|---|
| 3,853,896 | 12/1974 | Pessolano et al. | 546/157 |
| 4,006,237 | 1/1977 | Buckle et al. | 546/157 |
| 4,071,520 | 1/1978 | Wehrmeister | 546/157 |

OTHER PUBLICATIONS

Elderfield, Heterocyclic Compounds, vol. 4, pp. 129–137 (1952).

*Primary Examiner*—Donald G. Daus
*Assistant Examiner*—M. C. Eakin
*Attorney, Agent, or Firm*—Curtis, Morris & Safford

[57] ABSTRACT

8-Chloro-5,6,7,8-tetrahydro-2-quinolone and 8-bromo-5,6,7,8-tetrahydro-2-quinolone, the hydrochloride or hydrobromide thereof and their manufacture by reacting 3,4,5,6,7,8-hexahydro-2-quinolone with chlorine or bromine in an inert solvent at 10° to 50° C. with heating of the reaction mixture to 60° to 80° C. after the halogen addition.

12 Claims, No Drawings

8-CHLORO-5,6,7,8-TETRAHYDRO-2-QUINOLONE AND 8-BROMO-5,6,7,8-TETRAHYDRO-2-QUINOLONE, THE HYDROCHLORIDE OR HYDROBROMIDE THEREOF AND PROCESS FOR THEIR MANUFACTURE

This invention relates to 8-chloro-5,6,7,8-tetrahydro-2-quinolone and 8-bromo-5,6,7,8-tetrahydro-2-quinolone of the formula

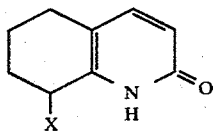

in which X denotes chlorine or bromine, and the hydrochloride or hydrobromide thereof, all of which have not yet been described in literature.

The invention also relates to a process for the manufacture of 8-chloro-5,6,7,8-tetrahydro-2-quinolone hydrochloride or 8-bromo-5,6,7,8-tetrahydro-2-quinolone hydrobromide, which comprises reacting 3,4,5,6,7,8-hexahydro-2-quinolone with chlorine or bromine in an inert solvent at a temperature of from 10° to 50° C. and heating the reaction solution to a temperature of from 60° to 80° C. when the halogen addition is terminated. The reaction with chlorine or bromine is preferably carried out at a temperature of from 25° to 40° C. and after termination of the halogen addition the temperature is preferably raised to 60° to 70° C.

The reaction takes place according to the following equation

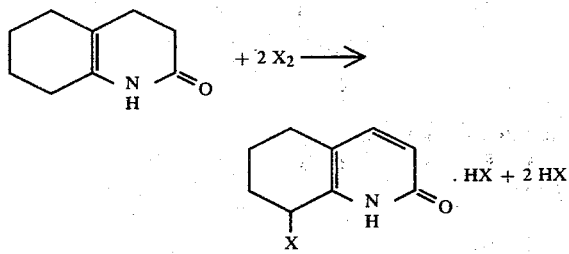

in which X denotes chlorine or bromine.

It is surprising that the reaction proceeds in one stage although it formally comprises two reaction steps, i.e. the halogenating dehydrogenation in 3,4-position and the halogenation in 8-position.

To isolate the free bases it is sufficient, for example, to heat the hydrohalide in an inert solvent such as xylene, dibutyl ether or monochlorobenzene to a temperature of from 120° to 150° C. whereupon the hydrogen halide escapes and the free 8-chloro-5,6,7,8-tetrahydro-2-quinolone (m.p. 192° C.) or 8-bromo-5,6,7,8-tetrahydro-2-quinolone (m.p. 166° C.) crystallizes upon cooling the solution.

Hence, the novel compounds can be obtained in a one-stage reaction from 3,4,5,6,7,8-hexahydro-2-quinolone, which, on its part, can be prepared in simple manner from cyclohexanone and acrylonitrile (cf. J. Org. Chem. 29, page 2781 (1964)).

The compounds according to the invention are very active halogen compounds and as such they can be used as starting products for the manufacture of a great number of derivatives. The reaction with aryl amines yields, for example, 8-arylamino-5,6,7,8-tetrahydro-2-quinolones which constitute valuable coupling components for the manufacture of polyester dyestuffs due to their high melting points (8-anilino-5,6,7,8-tetrahydro-2-quinolone, for example, melts at 225° C.).

In the reaction according to the invention preferably 1 to 4 mols of halogen, more preferably 2 to 3 mols of halogen, are used for each mol of starting compound. A higher halogen excess has, however, no detrimental effect on the yield of reaction product.

Suitable solvents for the starting compound to be halogenated are, in principle, all reaction-inert solvents such as chlorinated hydrocarbons, glacial acetic acid, dimethyl formamide. For an optimum separation of the reaction product solvents are preferred in which the final product is sparingly soluble, for example chlorinated hydrocarbons such as 1,2-dichloroethane, methylene chloride, chloroform, or carbon tetrachloride.

The use of 1,2-dichloroethane proved to be particularly advantageous since with its use the hydrohalides of the invention are directly obtained in a high purity.

In general, the concentration of the starting compound in the solvent is chosen in a manner such that one part by weight of starting compound is dissolved in 5 to 12 parts by volume, preferably 8 to 10 parts by volume of the respective solvent.

It proved advantageous for the halogenation reaction of the invention to maintain in relatively narrow limits the rate of introduction of gaseous chlorine or of liquid bromine. Advantageously, for each mol of dissolved starting compound a rate of introduction of chlorine or bromine of 0.2 to 0.6 mol, preferably 0.3 to 0.5 mol, of halogen per hour is chosen. This means that for 5 mols of starting compound from 1 to 3 mols of halogen per hour are preferred.

In general, the chlorine is not diluted, that is to say, a chlorine current is directly introduced into the solution of the starting compound, while the bromine is preferably diluted with the solvent used and the solution is added dropwise at the rate indicated above to the solution of the starting compound. In general, one part by volume of elemental bromine is diluted with 6 to 12 parts by volume, preferably 8 to 10 parts by volume, of the solvent used for the reaction.

During the after-heating to 60° to 80° C. according to the invention the 8-chloro-5,6,7,8-tetrahydro-2-quinolone hydrochloride or the 8-bromo-5,6,7,8-tetrahydro-2-quinolone hydrobromide separates in the form of crystals.

This fact constitutes a special advantage of the present process as any expenditure for the separation of byproducts can be dispensed with and the compounds of the invention can be isolated in simple manner.

The following examples illustrate the invention:

EXAMPLE 1

In a 1 liter flask 75.5 g (0.5 mol) of 3,4,5,6,7,8-hexahydro-2-quinolone (m.p. 147° C.) are dissolved in 400 ml of 1,2-dichloroethane and, at 33° to 35° C. and while stirring, 5 liters of chlorine are introduced per hour into the solution until the stoichiometric amount of chlorine has been absorbed within 4 hours.

To remove the hydrogen halide the temperature is gradually raised to 60° C. and the mixture is maintained at that temperature for 10 minutes until the escape of gas is terminated.

During heating crystalline reaction product separates from the solution. To remove dissolved hydrogen chloride still contained in the reaction mixture a dry current of air is blown through the suspension until it has cooled down to 25° to 30° C. The colorless crystals are filtered off with suction at 15° C. and washed with acetonitrile. 68 g of 8-chloro-5,6,7,8-tetrahydro-2-quinolone hydrochloride (m.p. 192° C.) are obtained, corresponding to a yield of 62% of the theory.

EXAMPLE 2

In a flask having a capacity of 500 ml 15.1 g (0.1 mol) of 3,4,5,6,7,8-hexahydro-2-quinolone are dissolved in 150 ml of 1,2-dichloroethane and at 35° C. a solution of 32 g of bromine in 100 ml of 1,2-dichloroethane is added dropwise over a period of 5 hours.

To remove hydrogen bromide the mixture is heated as described in Example 1.

The separated colorless crystals are filtered off with suction, and washed with acetonitrile. 14.5 g of 8-bromo-5,6,7,8-tetrahydro-2-quinolone hydrobromide melting at 160° C. are isolated, corresponding to a yield of 47% of the theory.

EXAMPLE 3

In a 2 liter flask 151 g (1.0 mol) of 3,4,5,6,7,8-hexahydro-2-quinonlon are dissolved in 800 ml of 1,2-dichloroethane and, at 34° C. to 35° C. and while stirring, 6.5 liters of chlorine are introduced into the solution per hour until the stoichiometric amount of chlorine has been absorbed within 7 hours.

The reaction mixture is further treated as described in Example 1. 154 g of 8-chloro-5,6,7,8-tetrahydro-2-quinolone hydrochloride are isolated, corresponding to a yield of 70% of the theory.

EXAMPLE 4

(a) Preparation of 8-anilino-5,6,7,8-tetrahydro-2-quinolone 110 g (0.5 mol) of 8-chloro-5,6,7,8-tetrahydro-2-quinolone hydrochloride are suspended in 800 ml of isopropanol and at 80° C. 186 g (2.0 mols) of aniline are added dropwise. A clear solution gradually forms which is refluxed for 10 minutes. The colorless crystalline 8-aniline-5,6,7,8-tetrahydro-2-quinolone separating on cooling is filtered off with suction and washed with acetonitrile. It is obtained in a yield of 94 g, corresponding to 78.3% of the theory and melts at 225° C.

(b) Coupling of 8-anilino-5,6,7,8-tetrahydro-2-quinolone 86 g of 2-chloro-4-nitroaniline are added to a mixture of 175 g of concentrated hydrochloric acid and 1000 ml of water and the mixture is stirred until a homogeneous suspension is obtained. After cooling to 10° C., 35 g of sodium nitrite are added and stirring of the mixture is continued for 45 minutes at 10° C. The solution of the diazonium salt is filtered, cooled to 0° to 5° C. and added while stirring to a solution of 120 g of 8-anilino-5,6,7,8-tetrahydro-2-quinolone in dilute acid and ice (236 g of concentrated hydrochloric acid and 500 g of water with ice). The mixture is neutralized to pH 5.5 to 6 first with sodium hydroxide solution and then with sodium acetate and the precipitate formed is filtered off with suction, washed and dried.

The dyestuff obtained in an amount of 202 g corresponds to the formula:

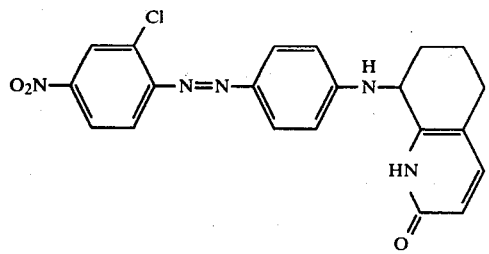

In organic solvents the red product dissolves to give an orange solution. In fine distribution the dyestuff dyes synthetic polyethylene terephthalate fabric orange tints having a good fastness to sublimation, to washing and to light.

What is claimed is:

1. 8-halo-5,6,7,8-tetrahydro-2-quinolone of the formula

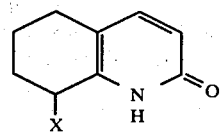

in which X is chlorine or bromine, and the hydrohalide thereof.

2. 8-Chloro-5,6,7,8-tetrahydro-2-quinolone of the formula

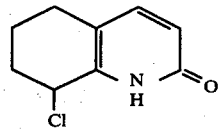

and its hydrochloride.

3. 8-Bromo-5,6,7,8-tetrahydro-2-quinolone of the formula

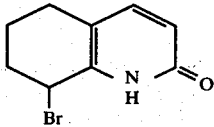

and its hydrobromide.

4. Process for the manufacture of 8-chloro-5,6,7,8-tetrahydro-2-quinolone hydrochloride or 8-bromo-5,6,7,8-tetrahydro-2-quinolone hydrobromide, which comprises reacting 3,4,5,6,7,8-hexahydro-2-quinolone with chlorine or bromine in an inert solvent and at a temperature of from 10° to 50° C. and heating the reaction solution to 60° to 80° C. after termination of the halogen addition.

5. The process claimed in claim 4, wherein the reaction with chlorine or bromine is effected at a temperature of from 25° to 40° C.

6. The process claimed in claim 4 or 5 wherein, after the halogen addition, the reaction solution is heated to 60° to 70° C.

7. The process of claim 4, wherein the inert solvent is a chlorinated hydrocarbon.

8. The process of claim 4, wherein the inert solvent is 1,2-dichloroethane.

9. The process of claim 4, wherein 0.3 to 0.5 mol of halogen per hour is used for each mol of 3,4,5,6,7,8-hexahydro-2-quinolone.

10. The process of claim 4, wherein 1 to 4 mols of halogen are used for each mol of 3,4,5,6,7,8-hexahydro-2-quinolone.

11. The process of claim 4, wherein the bromine is diluted with 6 to 12 times the volume of the inert solvent used for the reaction.

12. Process for the manufacture of 8-chloro-5,6,7,8-tetrahydro-2-quinolone or of 8-bromo-5,6,7,8-tetrahydro-2-quinolone, which comprises heating the hydrochloride of the former compound or the hydrobromide of the latter compound in an inert solvent and cooling the solution after escape of the respective hydrogen halide.

* * * * *